United States Patent [19]

Alroy et al.

[11] Patent Number: 5,437,986
[45] Date of Patent: Aug. 1, 1995

[54] EXTRACTION OF HETEROLOGOUS INSOLUBLE PROTEINS FROM BACTERIA

[75] Inventors: Yair Alroy, Parsippany; Jingdong Zhu, Westfield; Russell Condon, New Brunswick, all of N.J.

[73] Assignee: Schering Corporation, Kenilworth, N.J.

[21] Appl. No.: 263,961

[22] Filed: Jun. 22, 1994

[51] Int. Cl.⁶ ............... C12P 21/00; C12N 15/00
[52] U.S. Cl. ................... 435/71.2; 435/69.1; 435/69.52; 435/71.1; 435/172.3; 435/948; 530/351; 530/412; 530/420; 530/427; 530/825
[58] Field of Search ............ 435/71.2, 71.1, 69.1, 435/69.52, 172.3, 948; 530/351, 412, 427, 825, 420

[56] References Cited

U.S. PATENT DOCUMENTS

| | | | |
|---|---|---|---|
| 4,512,922 | 4/1985 | Jones et al. | 530/351 |
| 4,518,526 | 5/1985 | Olsen | 530/351 |
| 4,656,255 | 4/1987 | Seely | 530/412 |
| 4,748,234 | 5/1988 | Dorin et al. | 435/69.52 |
| 4,801,536 | 1/1989 | Stahl et al. | 435/69.1 |
| 4,958,007 | 9/1990 | Alroy et al. | 435/71.1 |
| 5,248,769 | 9/1993 | Dorin | 530/427 |

*Primary Examiner*—Herbert J. Lilling
*Attorney, Agent, or Firm*—Paul G. Lunn; Norman C. Dulak; James R. Nelson

[57] ABSTRACT

An insoluble mammalian protein is extracted from transformed bacteria expressing the mammalian protein while avoiding irreversible insolubilization of bacterial host proteins by homogenizing the fermentation broth, centrifuging the homogenized broth and removing the supernatant liquid for the inclusion body containing pellet. In another embodiment, the pH of the homogenized broth is adjusted to 2.0 prior to centrifugation. The acidified broth is then centrifuged, and the pellet is resuspended in buffer, homogenized again, and the inclusion body is isolated by centrifugation.

5 Claims, 1 Drawing Sheet

FIGURE 1/1
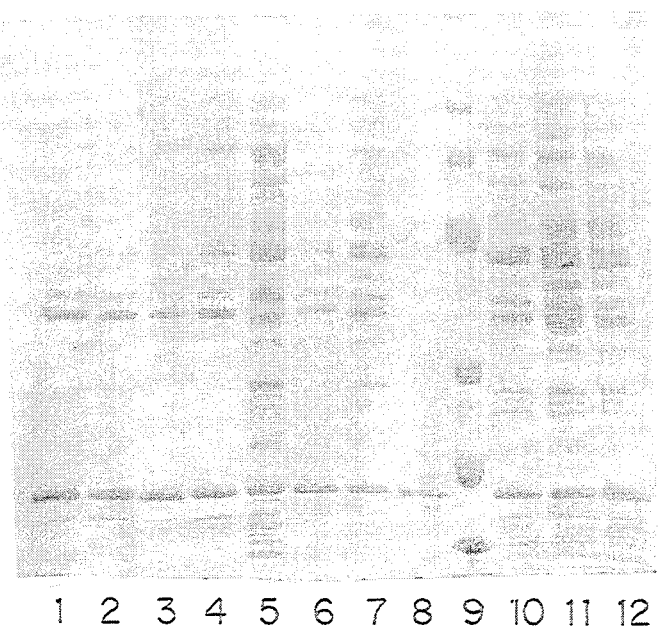
1 2 3 4 5 6 7 8 9 10 11 12

5,437,986

EXTRACTION OF HETEROLOGOUS INSOLUBLE PROTEINS FROM BACTERIA

BACKGROUND OF THE INVENTION

The transformation of bacteria with vectors containing DNA sequences encoding mammalian proteins is common. Expression of the mammalian proteins by bacteria can result in high production of the protein contained within inclusion bodies in the bacteria. To obtain and purify the protein, the protein-containing inclusion bodies must be extracted from the bacteria.

In the past inclusion bodies have been isolated by centrifuging the fermentation broth, removing the supernatant liquid, resuspending the bacterial pellet in buffer and disrupting the bacterial cells by mechanical techniques such as homogenization or sonication or, alternatively, by the use of lysozyme plus detergents. The mixture containing the disrupted cells is then centrifuged resulting in supernatant liquid and pelleted inclusion bodies. An inclusion body pellet is a pellet containing inclusion bodies obtained after bacterial cell disruption and subsequent centrifugation. However, this procedure involves centrifuging fermentation broth containing live bacteria as an initial step. Often, during large scale centrifugation the live bacteria can then be emitted into the surrounding atmosphere in the aerosol emitted by the centrifuge.

U.S. Pat. No. 4,958,007 solves this problem by first inactivating cells by adding either toluene or acid to the fermentation broth. The broth is then centrifuged, the supernatant liquid removed, and the bacterial pellet resuspended in a buffer and the pH of the suspension is adjusted such that the final pH is between 6-9. Alternatively, the pH of the acidified fermentation broth is adjusted to 6-9. The bacterial cells are then disrupted by homogenization releasing the inclusion bodies from the cells. This process eliminates the emission of live bacteria into the atmosphere during centrifugation; however, when toluene is used to inactivate the bacteria, the process must be carried out in an explosion-proof room as toluene is flammable and its fumes explosive. Furthermore, when acid is used to inactivate the bacteria and the bacterial pellet is resuspended in a buffer and the pH of the suspension is adjusted such that the final pH is between 6-9, previously soluble bacterial proteins are insolubilized resulting in an inclusion body pellet containing an unacceptably high level of bacterial host proteins.

Thus, there is a need for an improved process for extracting insoluble, recombinant proteins in which all or most of the bacteria are killed prior to centrifugation, most of the host bacterial proteins remain in solution, and the predominant insoluble protein is the bacterially expressed heterologous protein.

SUMMARY OF THE INVENTION

The present invention fills this need by disrupting the bacteria expressing the heterologous protein while the bacteria are still present in the fermentation broth followed by an optional inactivation of the bacteria by acid treatment. Centrifugation can then be performed without the emission of live bacteria. This bacterial disruption significantly lowers the count of viable bacteria, and at the same time it can be performed in a closed system to minimize or prevent emission of broth containing live bacteria. The methods of the present invention produce inclusion bodies containing a heterologous protein having increased purity, i.e. inclusion bodies having lower levels of insolubilized bacterial protein than is produced by extraction procedures of the prior art.

The present invention provides for three methods of extracting inclusion bodies containing heterologous protein from bacteria expressing the heterologous protein.

The first embodiment comprises the following steps:

(a) fermenting bacteria expressing a heterologous insoluble protein in a fermentation broth;

(b) disrupting the bacteria contained within the fermentation broth;

(c) centrifuging the fermentation broth so as to obtain an inclusion body pellet and a supernatant liquid; and (d) removing the supernatant liquid so as to obtain an inclusion body pellet.

The second embodiment of the invention comprises the following steps:

(a) fermenting bacteria expressing a heterologous insoluble protein in a fermentation broth;

(b) disrupting the bacteria contained within the fermentation broth;

(c) cooling or maintaining the fermentation broth at a temperature of 0°-15° C.;

(d) adding acid to the homogenized fermentation broth such that the fermentation broth obtains a pH of about 2.0;

(e) incubating the acidified fermentation broth at a temperature of between 0°-15° C. so as to kill any remaining undistrupted bacteria;

(f) centrifuging the fermentation broth so as to obtain an inclusion body pellet and a supernatant liquid;

(g) removing the supernatant liquid from the inclusion body pellet;

(h) suspending the inclusion body pellet in a buffer so as to obtain a suspension;

(i) adding a pH adjusting solution to the suspension so that the suspension obtains a pH of between 6-9;

(j) disrupting suspended solids contained within the suspension of step (i);

(k) centrifuging the suspension so as to produce an inclusion body pellet containing the heterologous protein and a supernatant liquid; and (l) removing the supernatant liquid so as to obtain isolated inclusion bodies containing heterologous protein.

The third embodiment of the present invention comprises the following steps:

(a) fermenting bacteria expressing a heterologous insoluble protein in a fermentation broth;

(b) disrupting the bacteria contained within the fermentation broth;

(c) cooling or maintaining the fermentation broth at a temperature of 0°-15° C.;

(d) adding nitric acid to the fermentation broth so that the broth obtains a pH of about 2.0;

(e) incubating the acidified fermentation broth at a temperature of between about 0°-15° C. so as to kill the bacteria;

(f) raising the pH of the broth to about 8.5;

(g) disrupting the broth;

(h) centrifuging the disrupted broth so as to produce an inclusion body pellet of inclusion bodies and supernatant liquid; and (i) removing the supernatant liquid so as to obtain isolated inclusion bodies containing heterologous protein.

BRIEF DESCRIPTION OF THE FIGURE

The file of this patent contains at least one drawing executed in color. Copies of this patent with color drawing(s) will be provided by the Patent and Trademark Office upon request and payment of the necessary fee. The FIGURE is an SDS-PAGE gel of inclusion bodies produced by the methods of the present invention and of inclusion bodies produced by methods other than by the present invention.

DETAILED DESCRIPTION OF THE INVENTION

All U.S. Patents cited herein are hereby incorporated herein in their entirety by reference.

The the present invention provides methods for extracting an insoluble, non-bacterial protein, in particular a mammalian protein produced by genetically transformed bacteria, especially *E. coli*. A non-bacterial protein which is expressed in bacteria is referred to as a heterologous protein. As used herein, the term "transformed bacteria" means bacteria that have been genetically engineered to produce a heterologous protein. Such genetic engineering usually entails the introduction of an expression vector into a bacterium. The expression vector is capable of autonomous replication and protein expression relative to genes in the bacterial genome. Construction of bacterial expression vectors is well known in the art, provided the nucleotide sequence encoding a desired protein is known or otherwise available. For example, DeBoer in U.S. Pat. No. 4,551,433 discloses promoters for use in bacterial expression vectors; Goeddel et al. in U.S. Pat. No. 4,601,980 and Riggs, in U.S. Pat. No. 4,431,739 disclose the production of mammalian proteins by *E. coli* expression systems; and Riggs supra, Ferretti et al. *Proc. Natl. Acad. Sci.* 83:599 (1986), Sproat et al., *Nucleic Acid Research* 3:2959 (1985) and Mullenbach et al., *J. Biol. Chem* 261:719 (1986) disclose how to construct synthetic genes for expression in bacteria. Many bacterial expression vectors are available commercially and through the American Type Culture Collection (ATCC), Rockville, Md.

The bacteria which have been transformed with an expression vector are then grown in a bacterial medium under conditions which stimulate the heterologous protein to be expressed. This bacterial medium containing the transformed bacteria is called a fermentation broth.

In the first embodiment of the present invention, the transformed bacteria, preferably a transformed *E. coli* strain, expressing a heterologous protein are disrupted by sonicating or homogenizing the fermentation broth by standard techniques at a temperature between 0° to 25° C. In general, sonication or homogenization of whole fermentation broth should proceed until essentially all the cells are broken. This allows efficient removal of soluble proteins and small cell fragments from the inclusion body by subsequent centrifugation; hence, it maximizes the protein's ultimate purity.

Sonication is generally used for disruption of bacteria contained in analytical (10–20 ml) scale volumes of fermentation broth. At larger scales high pressure homogenization should be used. For analytical volumes (10–20 ml) of fermentation broth using an Ultrasonic Processor Model No. W-85 from Heat-Systems-Ultrasonic, Inc., having a ⅛ inch (3.2 mm) tapered microtip, 18 minutes of total sonication time at 50% duty cycle, I second pulse (9 minutes net sonication) of 10 ml whole broth is preferred.

If homogenization is used to disrupt the bacteria, multiple passes of the fermentation broth are preferred. It has been observed that three passes of the fermentation broth through a MICROFLUIDIZER ® (Microfluidics M-110) at 11,000 pounds per square inch (psi) are adequate. During sonication or homogenization using a MICROFLUIDIZER ®, it is preferable to enclose the system such that emission of live bacteria is prevented. Large scale homogenizers are often set up in a closed system.

The sonicated or homogenized fermentation broth is then centrifuged to produce an inclusion body containing pellet and a supernatant liquid. The speed of the centrifugation should be sufficient to sediment most of the inclusion bodies but slow enough to keep most of the cell fragments in suspension within the supernatant liquid. In general the centrifugation should be from about 5000 rpm to 10,000 rpm, preferably 7000–10,000 rpm using an inch and one-half conical microcentrifuge tube in an EPPENDORF ® microcentrifuge Model No. 5402 for about ten minutes or equivalent. The supernatant liquid is then removed so as to obtain inclusion bodies containing the heterologous protein.

In the second embodiment of the present invention, after the bacteria within the fermentation broth have been disrupted, the temperature of the broth is reduced to 0°–15° C. The pH of the fermentation broth is then lowered to about 2.0 using sulfuric, phosphoric, nitric or hydrochloric acid at a temperature of about 0°–15° C. and then the broth is incubated at that temperature to kill any remaining bacteria, typically for about an hour. This is important because simple homogenization does not kill all of the bacteria. Preferably the acid which is used to lower the pH is either phosphoric or nitric acid. The fermentation broth is then centrifuged as described above, and the supernatant liquid removed to isolate the inclusion body pellet. The inclusion body pellet is then resuspended in a buffer. Examples of buffers which can be used in resuspending the pellet are sodium phosphate, potassium phosphate and tris (Hydroxymethyl) aminomethane hydrochloride (TRIS). A preferred buffer is comprised of 50 mM TRIS, 5 mM EDTA and 50 mM NaCl pH 8.5 (TEN buffer). The final pH of the resultant suspension is adjusted with a suitable base to a pH of between from about 6.0 to about 9.0, preferably 8.5. Examples of suitable bases that may be used in the pH adjustment step are sodium hydroxide, potassium hydroxide and the like. The preferred basic solution to raise the pH is a 25% w/v solution of NaOH.

The pH adjusted suspension is then disrupted again so as to disperse the solids present in suspension by sonication or homogenization, and it is subsequently centrifuged. Finally, the supernatant liquid containing the soluble host bacterial proteins and cell debris is removed, and the pellet containing the insoluble mammalian protein is recovered. If necessary, the pellet may be washed once or twice in buffer at a pH of preferably about 8.5. It is essential that the addition of acid be conducted between 0° and 15° C. All the other extraction operations may be carried out between 0° and 32° C.

In the third embodiment of the present invention the bacteria expressing the heterologous insoluble protein are fermented in a fermentation broth. The bacteria in the fermentation broth are disrupted by sonication or homogenization as described above. The temperature of the fermentation broth is then lowered to 0°–15° C., and nitric acid is added to the fermentation broth so as to lower the pH of the broth to about 2.0. The fermentation broth is then incubated at 0°–15° C. for a length of time necessary to kill any remaining bacteria, typically for about an hour.

The pH of the fermentation broth is then raised to about 8.5 and suspended solids including any remaining bacteria are again disrupted by homogenization or sonication. After this second disruption, the broth is centrifuged so as to produce a supernatant liquid and an inclusion body pellet. The supernatant liquid is then removed so as to obtain isolated inclusion bodies containing insoluble, heterologous protein.

In a large scale operation, the use of the acid kill procedures of embodiments 2 and 3 is preferred because the acid kill procedures easily kills essentially 100% of the bacteria. To kill 100% of the bacteria using homogenization alone is not cost effective, because of the multiple homogenization passes required to approach this goal.

After the inclusion bodies have been isolated, the heterologous protein can then be unfolded, refolded and purified using standard biochemical methods. See, for example, *Guide to Protein Purification*, Deutscher et al. Ed. (Academic Press, San Diego, Calif., 1990).

The following examples describe in detail the invention. It will be apparent to those skilled in the art that modification of materials and methods may be practiced without departing from the purpose and intent of the present disclosure.

The present invention can be illustrated by the following, non-limiting Examples. Unless otherwise specified, percentages given below for solids in solid mixtures, liquids in liquids, and solids in liquids are on a wt/wt, vol/vol and wt/vol basis, respectively.

EXAMPLE 1

(Embodiment 1 of the Present Invention)

The human IL-10 expression plasmid used in the present example contained the following sequences:

(a) The nucleotide sequence of the human IL-10 coding region, Viera, P., et al. *Proc. Natl. Acad. Sci. USA*, 88:1172 (1991);

(b) The tac promoter, the Y end of which was fused to the 5' end of the nucleotide sequence of the IL-10 coding region, Zurawski, et al., *J. Immunol.*, 137:3554 (1986);

(c) The Ipp 3' coding and non-coding regions, including the transcription terminator, lie downstream of the rhIL-10 coding region, Ghrayeb, J. et al., *EMBO, J.*, 3:2437 (1984).

(d) The tetracycline resistance gene from pBR322, Sutcliff, J. G., *C.S.H. Sypmp. Quant. Biol.* 135:612 (1978);

(e) The $cop^{TS}$ thermoinducible origin of replication, Hakkaart, M. J. J., et al., *Mol. Gen. Genet.* 83:326 (1981) and Andreoli, P. M., et al., *J. Bacteriol.* 135:612 (1978).

Fermentation

A culture of *E. coli* strain K12 harboring the above-described plasmid was cultivated under aeration and agitation in an aqueous fermentation medium. Each liter of medium contained 30 g of casamino acids (Difco) 20 g yeast extract (Difco), 5 g potassium dihydrogen phosphate, 20 g glycerol, 1 g $MgSO_4$ and 10 mg tetracycline (Sigma). The pH was controlled at 7.0 with 25% w/v of NaOH, and dissolved oxygen was maintained between 30–100% saturation with respect to air under 5 psi pressure. The temperature was initially controlled at 30° C. When the culture's turbidity reached about 100 Klett units as measured with a Klett Summerson colorimeter having a No. 54 green filter, the temperature was raised to about 38° C., and the culture was harvested 12–14 hours thereafter.

Extraction

The whole fermentation broth was passed three times through a MICROFLUIDIZER M-110 ® homogenizer (Microfludics, Inc.) under about 11,000 psi pressure to disrupt the cells. The homogenizer and product containers were kept on ice so the temperature of the homogenized suspension was kept between 0°–15° C.

The fermentation broth temperature was then reduced to 4° C. and agitated for about an hour at pH 7. The suspension was then centrifuged in 250 ml aliquots at 8,000 rpm for 65 minutes in a GS-3 head of a SORVAL ® centrifuge (model RC5C) at 4° C. The supernatant was discarded and the extracted IL-10 remained in the pellet. The purity of the resulting inclusion bodies is shown by sodium dodecyl sulfatepolyacrylamide gel electrophoresis (SDS-PAGE), Laemmli, U.K., *Nature*, 227: 680 (1970) in lane 1, FIG. 1. According to this process, the inclusion bodies were resuspended in a buffer to a concentration equivalent to 15 $OD_{550}$ of original broth in a 1 cm light path. The buffer was comprised of 2.3% sodium dodecyl sulfate (SDS), 10% glycerol, 0.062M Tris-HCl pH 6.8, 0.001% bromophenol blue and 5% β-mercaptoethanol (freshly added). 10 μl was then loaded in each well of a DAIICHI mini gradient gel (12 wells total). The gel was run in a running buffer under a constant current, 35 mA/gel. When the blue dye reached the bottom of the gel the current was stopped and the gel was developed as described by Laemmli, above. The results are shown in lane 1 of the Figure.

EXAMPLE 2

(Embodiment 2 of the Present Invention)

IL-10 containing inclusion bodies were prepared as described in Example 1 except for the following. After the fermentation broth was homogenized, as in example 1, the temperature of the broth was reduced to 4° C. and the pH of the broth was lowered to 2.0 by adding 85% w/w phosphoric acid. The acidified suspension was then agitated for about an hour at 4° C. The acidified suspension was then centrifuged in 250 ml aliquots at 8,000 rpm for 65 minutes in a GS-3 head of a SORVAL ® centrifuge (model RC5C) at 4° C. The supernatant liquid was discarded, and the inclusion body pellet was resuspended to ¼ of the original fermentation broth volume with TEN buffer and the pH of the buffer was raised to 8.5 with a solution of 25% NaOH. The resultant suspension was passed three times through a MICROFLUIDIZER M-110 ® and centrifuged in a GS-3 head of a SORVAL centrifuge as described above. The supernatant was discarded and the extracted IL-10 remained in the pellet.

The purity of the resulting inclusion bodies is shown by SDS-PAGE in lane 2 of the FIGURE.

EXAMPLE 3

(Embodiment 2 of the Present Invention)

IL-10 containing inclusion bodies were prepared as described in Example 2 except for the following. A solution of 9N HNO$_3$ was used instead of phosphoric acid to reduce the pH of the fermentation broth to 2.0.

The purity of the resulting inclusion bodies is shown by SDS-PAGE) in lane 3, of the FIGURE.

EXAMPLE 4

(Embodiment 2 of the Present Invention)

IL-10 containing inclusion bodies were prepared as described in Example 2 except for the following. A solution of 9N H$_2$SO$_4$ was used instead of phosphoric acid to reduce the pH of the fermentation broth to 2.0.

The purity of the resulting inclusion bodies is shown by SDS-PAGE in lane 4 of the FIGURE.

EXAMPLE 5

(Not an embodiment of the present invention)

IL-10 containing inclusion bodies were prepared as described in Example 2 using 85% w/w phosphoric acid to acidify the homogenized broth except for the following. After the acidified suspension had been agitated for an hour, the pH of the suspension was raised to 8.5 with 25% w/v NaOH solution. The suspension was passed three times through a MICROFLUIDIZER M-110® and centrifuged in 250 ml aliquots at 8,000 rpm for 65 minutes in a GS-3 head of a SORVAL® centrifuge (model RC5C) at 4° C. The supernatant was discarded and the extracted IL-10 remained in the pellet.

The purity of the resulting inclusion bodies is shown by SDS-PAGE) in lane 5 of the FIGURE.

EXAMPLE 6

(Embodiment 3 )

IL-10 containing inclusion bodies were prepared as described in Example 5 except for the following. A solution of 9N HNO$_3$ was used to reduce the pH of the fermentation broth to 2.0.

The purity of the resulting inclusion bodies is shown by SDS-PAGE in lane 6 of the FIGURE.

EXAMPLE 7

(Not an embodiment of the present invention)

IL-10 containing inclusion bodies were prepared as described in Example 5 except for the following. A solution of 9N H$_2$SO$_4$ was used to reduce the pH of the fermentation broth to 2.0.

The purity of the resulting inclusion bodies is shown by SDS-PAGE in lane 7 of the FIGURE.

EXAMPLE 8

(Not an embodiment of the present invention)

Lane 8 shows the purity of IL-10 produced and purified from Chinese Hamster Ovaries as described in International Patent Application PCT/US94/01909. The purity was determined by SDS-PAGE of the FIGURE as described in Example I except that a 20µl sample was loaded into the well.

EXAMPLE 9

(Not an embodiment of the present invention) Lane 9 shows a high molecular weight standard marker used to estimate the molecular weight of the proteins in the other lanes of the FIGURE.

EXAMPLE 10

(Prior Art)

The bacteria producing the IL-10 were fermented as in example 1. When the fermentation was completed, the pH of the fermentation broth was reduced to 2.0 with 9N HNO$_3$ and agitated for 1 hour. The pH of the broth was raised to 8.5 with 25% w/v NaOH. The resultant suspension was passed three times through a MICROFLUIDIZER M-110® and centrifuged in a GS-3 head of a SORVAL® centrifuge as described above. The supernatant was discarded and the extracted IL-10 remained in the pellet.

The purity of the resulting inclusion bodies is shown by SDS-PAGE in lane 10 of the FIGURE.

EXAMPLE 11

(Prior Art)

IL-10 containing inclusion bodies were prepared as described in Example 10 except for the following. A solution of 9N H$_2$SO$_4$ was used to reduce the pH of the fermentation broth to 2.0.

The purity of the resulting inclusion bodies is shown by SDS-PAGE in lane 11 of the FIGURE.

EXAMPLE 12

(Prior Art)

IL-10 containing inclusion bodies were prepared as described in Example 10 except for the following. A solution of 85% w/w H$_3$PO$_4$ was used to reduce the pH of the fermentation broth to 2.0.

The purity of the resulting inclusion bodies is shown by SDS-PAGE) in lane 12 of the FIGURE.

Conclusion

FIG. 1 illustrates the surprising ability of the embodiments of the present invention to produce inclusion bodies having low levels of impurities, i.e., low levels of insoluble host proteins. The first lane is the SDS-PAGE gel of the inclusion bodies containing IL-10 extracted during Example 1 which is method of the first embodiment of the present invention. The fermentation broth containing the bacteria was homogenized and centrifuged to produce isolated, clean inclusion bodies.

The purity of inclusion bodies produced by the second embodiment of the present invention is illustrated by lanes 2, 3 and 4 of FIG. 1. Lanes 2, 3 and 4 are inclusion bodies produced according to Examples 2, 3 and 4 respectively in which the homogenized fermentation broth was acidified, incubated at a temperature between 0–15° C. and centrifuged to produce an inclusion body pellet and supernatant liquid. The pellet is resuspended in a buffer; the pH raised to 8.5 and the suspension homogenized. The suspension was then centrifuged again and the inclusion pellet isolated. Example 2 (lane 2) used phosphoric acid, Example 3 (lane 3) used nitric acid, and Example 4 used sulfuric acid to acidify the homogenized broth. As FIG. 1 clearly illustrates, the process of the second embodiment of the present invention produces inclusion bodies having a high degree of purity.

Lane 6, produced by the process of Example 6, shows the SDS-PAGE gel of the inclusion bodies produced according to the process of the third embodiment of the present invention. In this embodiment, the pH of the homogenized fermentation broth was lowered to about 2.0 with nitric acid, and agitated for about an hour at a temperature between 0°–15° C. The pH of the broth was then raised to about 8.5. The broth was then homogenized again and centrifuged to produce the isolated inclusion bodies. According to the third embodiment of the invention only nitric acid was effective in producing clean inclusion bodies. If either phosphoric acid, Example 5, lane 5, or sulfuric acid, Example 7, lane 7 were substituted for nitric acid, inclusion bodies containing unacceptably high levels of insoluble bacterial host proteins were produced.

Lane 8 is an SDS-PAGE gel of human IL-10 produced by Chinese Hamster Ovary (CHO) cells. Lane 9 is an SDS-PAGE gel of a high molecular weight standard. Lanes 10, 11 and 12 show. SDS-PAGE gels of inclusion bodies produced according to prior art methods described in Examples 10, 11 and 12 respectively, showing that the prior art methods of extracting heterologous proteins from bacteria produce inclusion bodies having substantially higher levels of host proteins than inclusion bodies extracted according to the processes of the present invention.

In summary, all of the embodiments of the present invention produce cleaner inclusion bodies as illustrated by lanes 1, 2, 3, 4 and 6 of FIG. 1, while the inclusion bodies produced by other methods result in inclusion bodies having unacceptably high levels of host protein.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention, which is only to be limited by the claims.

What is claimed is:

1. A method of extracting a heterologous protein from bacteria expressing said heterologous protein comprising the following steps:
   (a) fermenting the bacteria in a fermentation broth;
   (b) disrupting the bacteria contained in the fermentation broth;
   (c) cooling or maintaining the fermentation broth at a temperature of between about 0°–15° C.;
   (d) adding an acid to the fermentation broth such that the fermentation broth obtains a pH of about 2.0;
   (e) incubating the acidified fermentation broth at a temperature of between 0°–15° C. so as to kill any remaining undisrupted bacteria;
   (f) centrifuging the fermentation broth so as to obtain an inclusion body pellet and a supernatant liquid;
   (g) removing the supernatant liquid from the inclusion body pellet;
   (h) suspending the inclusion body pellet in a buffer so as to obtain a suspension;
   (i) adding a pH adjusting solution to the suspension so that the suspension obtains a pH of between 6–9;
   (j) disrupting suspended solids contained within the suspension of step (i);
   (k) centrifuging the suspension so as to produce an inclusion body pellet containing the heterologous protein and a supernatant liquid; and
   (l) removing the supernatant liquid so as to obtain isolated inclusion bodies containing heterologous protein.

2. The method of claim 1 wherein the acidified fermentation broth is maintained at a temperature of 0°–25° C.

3. The method of claim 1 wherein the acidified fermentation broth of step (d) is incubated for about an hour prior to centrifugation at a temperature between 0°–15° C.

4. The method of claim 1 wherein the acid is selected from the group consisting of phosphoric acid, nitric acid, hydrochloric acid and sulfuric acid.

5. A method of extracting a heterologous protein from bacteria expressing said heterologous protein consisting essentially of the following steps:
   (a) fermenting the bacteria in a fermentation broth;
   (b) disrupting the bacteria contained in the fermentation broth;
   (c) cooling or maintaining the fermentation broth at a temperature of between about 0°–15° C.;
   (e) adding nitric acid to the fermentation broth such that the fermentation broth obtains a pH of about 2.0;
   (f) incubating the acidified fermentation broth at a temperature of between 0°–15° C. so as to kill the bacteria;
   (g) raising the pH of the broth to about 8.5;
   (h) disrupting and dispersing solids contained within the broth;
   (i) centrifuging the fermentation broth so as to produce a supernatant liquid and inclusion body pellet containing inclusion bodies; and
   (j) removing the supernatant liquid so as to obtain isolated inclusion bodies containing the heterologous protein.

* * * * *